United States Patent [19]

Blesener et al.

[11] Patent Number: 5,121,988
[45] Date of Patent: Jun. 16, 1992

[54] SINGLE PARTICLE DETECTOR METHOD AND APPARATUS UTILIZING LIGHT EXTINCTION WITHIN A SHEET OF LIGHT

[75] Inventors: James L. Blesener, White Bear Lake; Stanley L. Kaufman, Minneapolis; David B. Blackford, St. Paul; Frank D. Dorman, Minneapolis; Peter P. Hairston, St. Paul, all of Minn.

[73] Assignee: TSI Incorporated, St. Paul, Minn.

[21] Appl. No.: 416,958

[22] Filed: Oct. 4, 1989

[51] Int. Cl.⁵ .................. G01N 15/06; G01N 15/14
[52] U.S. Cl. ........................ 356/442; 356/335; 250/574
[58] Field of Search ............ 356/442, 338, 336, 337, 356/246, 335, 438, 439, 440, 386, 389; 250/574, 575, 222.1, 222.2

[56] References Cited

U.S. PATENT DOCUMENTS

| | | | |
|---|---|---|---|
| 3,548,655 | 12/1970 | Rudd | 73/194 |
| 3,851,169 | 11/1974 | Faxvog | 250/222 |
| 4,739,177 | 4/1988 | Borden | 356/338 |

FOREIGN PATENT DOCUMENTS

| | | |
|---|---|---|
| 58-18149 | 4/1983 | Japan . |
| 60-140141 | 7/1985 | Japan . |
| 63-50739 | 3/1988 | Japan . |
| 1129138 | 5/1989 | Japan . |
| 0883714 | 10/1981 | U.S.S.R. ............ 356/246 |
| 1222177 | 2/1971 | United Kingdom . |

Primary Examiner—Vincent P. McGraw
Assistant Examiner—LaCharles P. Keese, II
Attorney, Agent, or Firm—Merchant, Gould, Smith, Edell, Welter & Schmidt

[57] ABSTRACT

A particle flux counter apparatus utilizing light extinction. The apparatus utilizes two oppositely disposed cylindrical mirrors (21a, 21b) to bounce a beam back and forth between them, the beam traversing the length of the cylindrical mirrors (21a, 21b) in incremental steps. A plane mirror (22) is cooperatively located to reflect the beam back between the system to traverse the length of the cylindrical mirrors (21a, 21b) a second time in incremented steps. The two sets of steps interleaving such that the beam forms a sheet of light. A detector (60) monitors the intensity of the beam. As particles in a sample aerosol intersect the beam, the light is extinguished and the beam intensity changes. The detector (60) transmits a signal to a microprocessor (108) analyzation. The apparatus also utilizes a feedback circuit (300) to regulate the beam intensity and alternatively provides for modulating the beam to provide for higher peak power into the detector (60) and elimination of common mode noise.

8 Claims, 12 Drawing Sheets

FIG.4
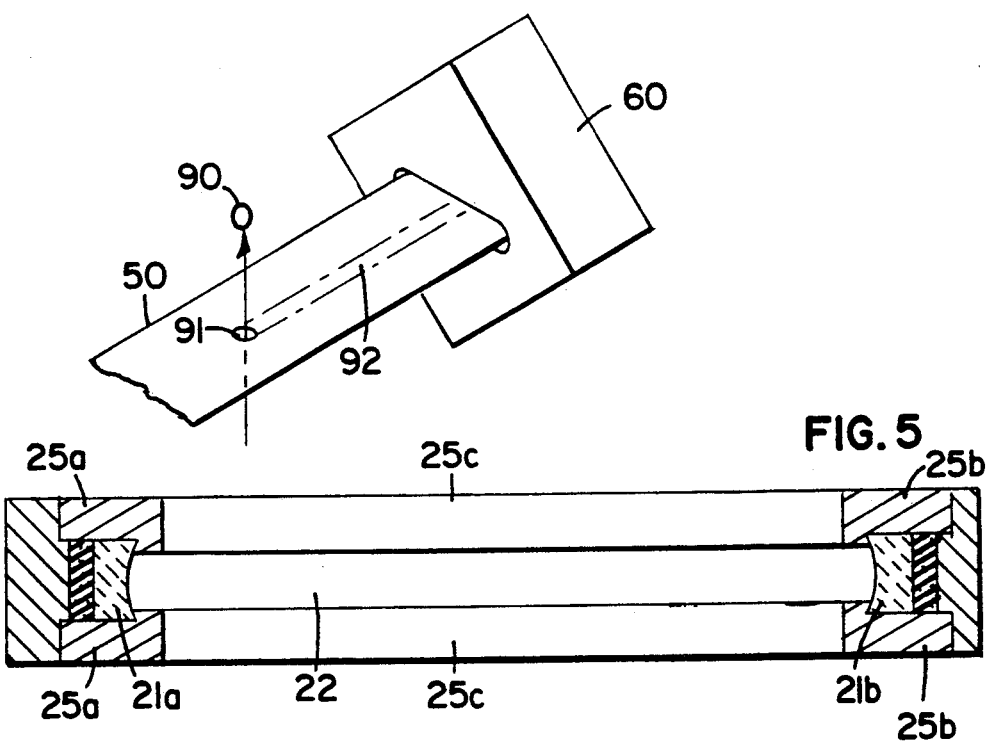
FIG.5
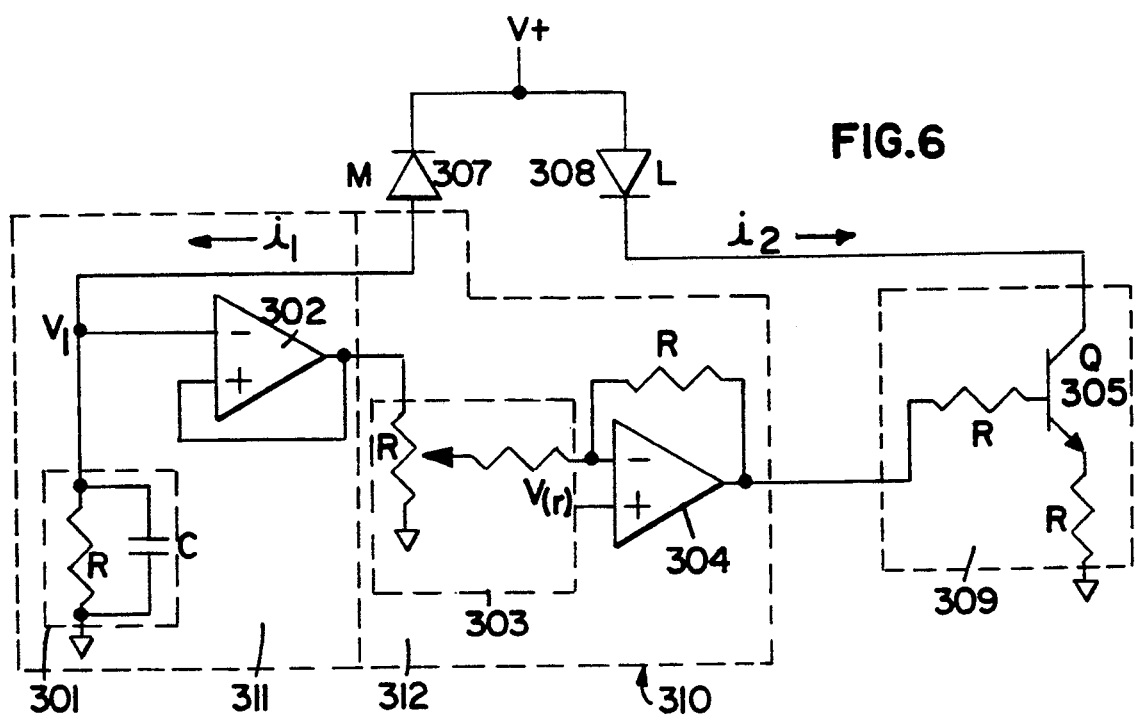
FIG.6

SINGLE PARTICLE DETECTOR METHOD AND APPARATUS UTILIZING LIGHT EXTINCTION WITHIN A SHEET OF LIGHT

FIELD OF THE INVENTION

This invention relates generally to the detection of particles, and more specifically to a method and apparatus for the detection of single particles intersecting a light sheet utilizing light extinction.

BACKGROUND OF THE INVENTION

Airborne contamination in the form of large particles (e.g. greater than 10 μm) is difficult to measure due to known limitations associated with sampling. As particle size increases, the distribution of particles entrained in a given air flow changes due to the momentum of the larger particles' mass overcoming the entraining forces of the air flow (i.e., the number of particles of a given size may decrease, thereby changing the distribution). Since the entraining forces are not large enough to change the particle direction, impaction of particles on the sampling device's inlet nozzle tends to occur. The impaction phenomenon versus particle size skews the results and, thereby, the counting efficiency.

Particle impaction phenomenon is distinct, however, and can therefore be used as a sampling technique in and of itself. At least one device utilizes large particle impaction for measuring aerosols. The device is manufactured by Berkeley Controls Inc., of Laguna Beach, California, having a model designation C-1000A QCM. The device may be considered a cascade impactor which creates an air flow through a system of impactor plates. Each impactor has a certain aerodynamic design which allows particles of less than a certain aerodynamic diameter to "follow", or be entrained by, the air flow through the device and not be impacted. Particles above the certain aerodynamic diameter do not follow the air flow path and are impacted on an impactor plate. Therefore, each of the plates are designed to capture particles of a certain size and above. In the case of the above identified model, there are 11 cascaded impacters, each with its own size limit for impaction.

The concentration of particles in the cascade impactor is determined by measuring the frequency response of crystals, located on the impactors. The mass of the impacted particles on the impactor plate causes the crystals' frequency to shift, from which certain information regarding the particles may be determined. Although this particular device has the advantage of being able to measure the concentration of particles while sampling (i.e., real time measurement), most impactor style devices are designed such that the impactor plate must be weighed after a sample is taken in order to calculate a concentration.

In general, impactor style devices have several disadvantages. First, size is a disadvantage. If real time measurements are needed, the device is typically quite large. Second, the impactor surfaces become contaminated with impacted particles and need to be cleaned and serviced regularly. Third, when an impactor is used, there arises the need to pull a particle laden sample airflow through the device. In many cases pulling an artificial sample airflow disturbs particle distribution and skews the results. Fourth, the device has an inherent inability to measure particle concentrations accurately due to the finite resolution of the particle impaction system.

U.S. Pat. No. 4,739,177 describes another type of large particle detection sensor, offering many advantages over the above described impactor design. The disclosed sensor bounces a collimated laser beam back and forth a selected number of times between two mirrors such that the beam creates a light net. The beam is terminated at the end of the system. The sensor has an open cavity defining a flow volume through which the test sample passes, with the mirrors being located on two opposing edges of the flow volume. The area between the mirrors defines a sampling volume, with the area covered by the laser beam defining a viewing volume. Particles which pass through the viewing volume intersect the beam, thereby scattering light. The scattered light is collected and converted to a corresponding particle size based on the collected amount of scattered light.

This type of sensor offers several advantages over the above described impactor designs. First, it has an open cavity (i.e., flow volume) for particle detection and, therefore, needs no pump for pulling a sample through the sensor. Second, it does not use an impactor design and, therefore, does not need frequent cleaning and servicing.

An example of the type of sensor disclosed in U.S. Pat. No. 4,739,177 is manufactured by High Yield Technology, of Mountainview, California, designated model PM-100. The sensor exhibits a disadvantage in that the beam of light does not cover one-hundred percent of either the flow or sampling volumes. Instead, the sampling volume only covers 50% of the flow volume. Further, the viewing volume is only 36% of the flow volume. Therefore, only 18% of the sample aerosol moving through the sensor's flow volume is actually sampled.

Another disadvantage of this device is the limited counting efficiency of particles actually in the viewing volume. Only 13% of the 6 μm particles in the viewing volume are counted due to the fundamental operating limits of the device (i.e., scattered light collection limitations, among others). Therefore, the device's theoretical efficiency is only 4.7% for 6 μm particles passing through the sample volume (See Rob Caldow, *Performance of The High Yield Technology PM-100 Particle Flux Monitor*, M.S.M.E. Thesis, (1987)).

A third disadvantage of this latter style sensor is that it collects the scattered light from the particles. In optical particle counters, scattered light is considered to be the light which is directed out of the path of the beam. As disclosed in U.S. Pat. No. 4,739,177, scattered light has many angular dependencies and thus causes a signal output which is not a linear function of particle size.

Light extinction, however, is considered to be the light which is removed from the beam path. The extinction function for large particles is quadratic with respect to the particle's diameter, or is a linear function for the projected area of large particles and thus allows for a more accurate device in large particle size ranges. Further, extinction techniques are less sensitive to stray light from other sources than are scattered light devices. Still further, use of extinction eliminates the need for collector optics.

Therefore, as can be appreciated, there arises a need for a method and device for producing real time, continuous measurements of particles. This device should allow for maximizing actual sampling of the flow and sample volumes and for maximizing counting efficiency of the particles moving through the sample volume. The device should also detect single particles, include means for solving inherent sampling problems, and allow for a large fluctuation in sample flow rates without adversely affecting the device's particle detection characteristics.

SUMMARY OF THE INVENTION

A preferred embodiment of an apparatus constructed according to the principles of the present invention includes a particle detector which provides for creating a sheet of light comprising a sensing volume and provides for detecting, by means of light extinction, single particles intersecting the sensing volume. The apparatus detects concentration, size and velocity of the particles. In a preferred embodiment, a device constructed according to the principles of the present invention includes a laser light source and beam shaping optics to form a wide, flat beam. The beam enters into a mirror cavity and covers one-hundred percent (100%) of the cavity by overlapping. The mirror cavity forms the overlapping coverage by reflecting the beam back and forth between mirrors from a first end of the cavity to a second end and back to the first end, the beam then exiting the cavity onto a detector. The detector monitors received light intensity and is arranged and configured to detect intensity changes. When particles intersect the beam, light in the beam path is "blocked out" or extinguished from the beam path and thereby light incident on the detector is decreased, thereby affecting the incident light intensity. Means are provided to electronically convert the intensity change to count the particle and to determine particle size and velocity.

In a preferred embodiment particle counter, the counter is placed such that natural aerosol flows pass through the counter's flow volume (i.e., the counter's cavity). The counter's flow volume is arranged and configured to essentially define the counter's sample and viewing volumes (i.e., the entire aerosol flow moving through the flow volume is effectively sampled and the coverage of tested aerosol flow is thereby maximized). Since a sheet of light is utilized to cover the entire flow volume, the area sampled between the mirrors will be referred to herein as the effective sensing volume. Preferably the bounds of the sensing volume are comprised of two cylindrical mirrors oppositely disposed from one another; a flat mirror, oriented between the two-cylindrical mirrors, which forms a third edge; and the fourth edge defined by beam shaping optics, detection means and components of the counter's housing.

The cylindrical mirrors are preferably arranged and configured to reflect the beam back and forth between the cylindrical mirrors a selected number of times so as to cause an advancing of successive reflections on the mirror surface in incremental steps. Therefore, each incremental step reflection occurs at a predetermined distance from the previous reflection, and so on down the longitudinal reflective length of the cylindrical mirrors (i.e., the mirrors' radius of curvature is considered herein as its transverse surface and the mirrors longer reflective surface which bounds the sensing volume is considered the longitudinal length). The flat mirror then reflects the beam back into the sensing volume such that the beam once again reflects back and forth between the cylindrical mirrors in a second set of incremental steps. This second set of steps travels "up" the longitudinal length filling in the "gaps" created by the first incremental steps, thereby forming a complete sheet of light covering the flow volume. A three-axis steering mirror is used to direct the beam from its source into the sensing volume.

Therefore, according to one aspect of the invention, there is provided a particle flux counter, of the type wherein a sample aerosol passes through a sensing volume, and wherein particles in the sample aerosol extinguish light when intersecting the sensing volume, the particle detector comprising:

a) a light source for creating a beam of light;

b) means for directing said beam of light through the sensing volume, wherein said sensing volume is defined as the intersection of said beam of light and the sample aerosol; and c) means for receiving said beam of light after said beam of light passes through the sensing volume and for detecting changes in light intensity in said beam of light, whereby changes in light intensity indicate the presence of a particle in the sample aerosol.

According to another aspect of the invention, there is provided means for reflecting the beam back into the sensing volume so as to form a sheet of light and onto said detector means, whereby the sensing volume equals the viewing volume.

Yet according to another aspect of the invention there is provided a particle counter for detecting particles in a fluid, of the type wherein a sample fluid passes through a laser beam, the intersection of the fluid and beam forming a sensing volume, and wherein particles suspended in the fluid extinguish light from the beam when the particles intersect the sensing volume, the particle counter comprising:

(a) a laser diode, said laser diode having a first and a second lasing facet, said laser diode generating a first beam emerging from said first lasing facet when forward biased and said laser diode generating a second beam emerging from said second lasing facet related to said first beam;

(b) means for focusing said first beam and directing said first beam through said sensing volume;

(c) feedback means for generating an error signal responsive to the intensity of said second beam;

(d) laser drive means, cooperatively connected to said first and second laser facets and said feedback means, for receiving said error signal and supplying a drive signal to said first and second laser facets wherein said error signal is reduced and the intensity of said first beam is stabilized; and (e) detector means, arranged and configured so as to normally lie in the path of said first beam after said first beam has intersected said sensing volume, for receiving said first beam and detect intensity changes in said first beam, whereby intensity changes indicate the presence of particles.

Further, according to the latter described invention there is provided another aspect wherein the laser drive means is a transistor with its collector tied to said first and second lasing facets and its base tied to said feedback means.

Still further, according to the latter described invention there is provided another aspect wherein the feedback means comprise:

(a) a resistor capacitor network for establishing a frequency response and a voltage level for power control;

(b) buffer means for isolating said voltage level;

(c) voltage divider means for reducing said voltage level; and (d) comparator means for comparing said reduced voltage level to a reference level and providing an error signal and baseline power control to said transistor.

While the invention will be described with respect to a preferred embodiment configuration and with respect to particular components used therein, it will be understood that the invention is not to be construed as limited in any manner by either such configuration or components.

These and various other advantages and features are pointed out in the claims annexed hereto and forming a part hereof. However, for a better understanding of the invention, its advantages and objectives obtained by its use, reference should be made to the Drawing which forms a further part hereof and to the accompanying descriptive matter, in which there is illustrated and described a preferred embodiment of the invention.

BRIEF DESCRIPTION OF THE DRAWING

Referring to the Drawing, wherein like numbers represent like parts throughout the several figures:

FIG. 4 is an unscaled diagrammatic illustration of large particle light extinction phenomena;

FIG. 5 is a cross section taken through line 5—5 of FIG. 1;

FIG. 6 is an electrical schematic diagram illustrating functional elements of the electronics of a preferred laser feedback circuit labeled block 300 of FIG. 2;

FIG. 8b is the partially exploded view of a portion of the counter of FIG. 8a;

FIG. 9c is a cross section of the beam 50 taken through line 9c-9c of FIG. 9a;

FIG. 13b is a functional block diagram of the signals utilized in the alternative embodiment of FIG. 13a.

DETAILED DESCRIPTION OF THE INVENTION

The principles of the present invention apply particularly well to its application to a particle detection device utilizing light extinction. The preferred embodiment of the present invention is compact in design and its elements interact with each other to make an efficient, reliable measurement instrument. Although described herein in connection with a preferred embodiment device utilizing a light sheet forming an effective sensing volume and further utilizing natural aerosol flows, the invention is not so limited.

A. General Overview

Figure 1:
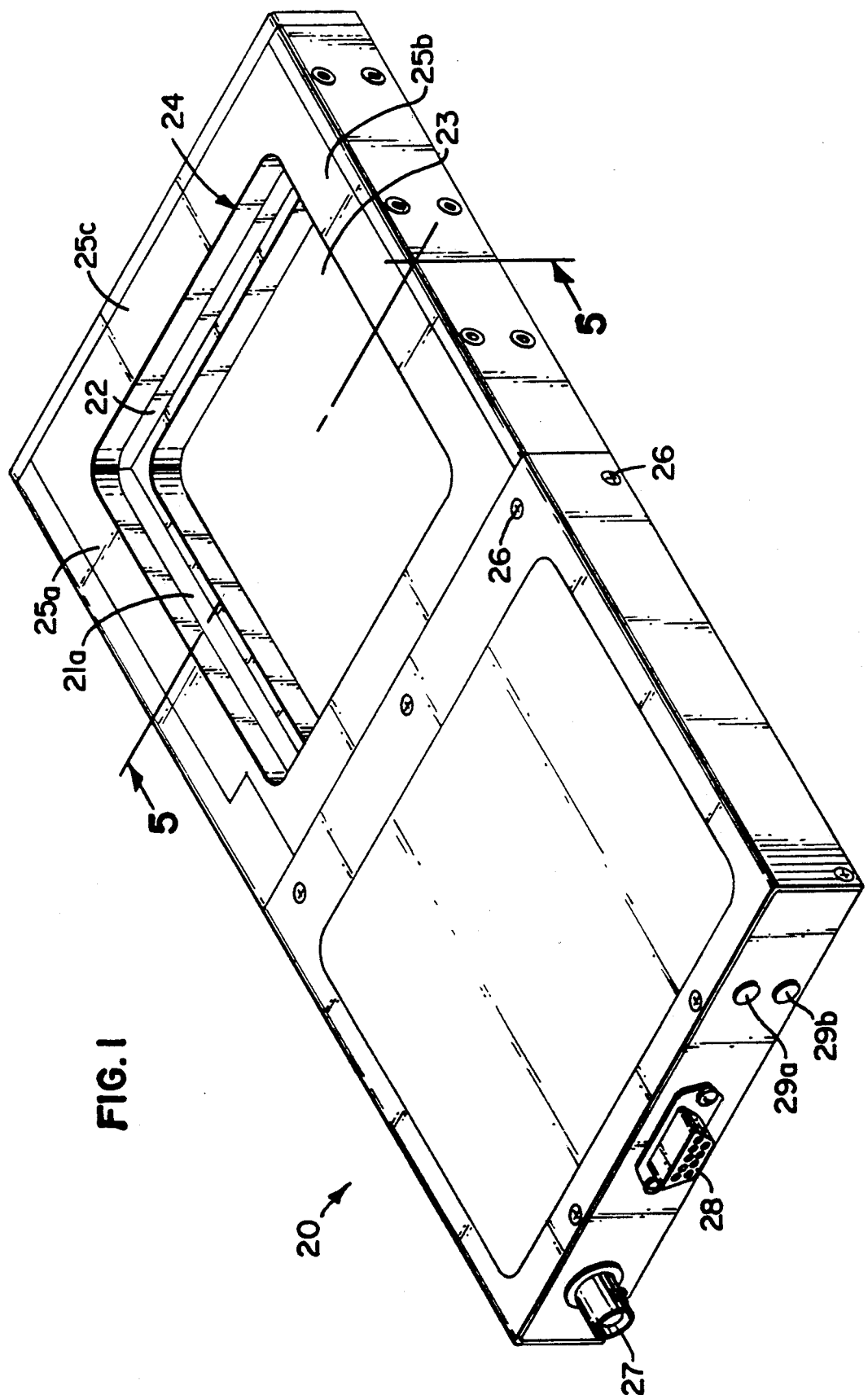
FIG. 1 is a perspective view of a particle flux counter constructed according to the principles of the present invention.

Referring first to FIGS. 1 and 5, there is illustrated an example of a preferred embodiment of a particle flux counter device. The counter is illustrated generally at 20. The counter 20 includes a cavity, or void, 23 bounded by overlapping edge 24. The void 23 (hereafter referred to as effective sensing volume 23 (ESV)) defines the counter's 20 flow volume by providing an area through which sample aerosols may pass through the counter 20. It will become apparent to those skilled in the art that in the preferred embodiment, the counter's 20 flow volume is completely covered by the counter's 20 sample and viewing volumes. As noted above, the flow volume is equivalent to the counter's effective sensing volume 23, thereby providing maximized coverage of the sampled aerosol.

Cylindrical mirrors 21a, 21b (21b best seen in FIG. 5) are cooperatively mounted on side edges 25a, 25b of counter 20 respectively, and are preferably recessed within side edges 25a, 25b (best seen in FIG. 5) so as to minimize blocking or impeding the free stream air flow. By recessing the cylindrical mirrors 21, protection is provided to the reflective surfaces of the cylindrical mirrors 21, as well as ensuring that the entire flow volume is sampled by the sensing volume (described further below).

Cooperatively located at one longitudinal end of the oppositely disposed cylindrical mirrors 21 is flat mirror 22. Flat mirror 22 is similarly recessed in side edge 25c of counter 20 to protect its surface and provide full sampling coverage of the ESV 23. Processor port 27 is provided at the end opposite the counter's 20 ESV 23. An RS-232 interface 28 provides a serial communications port and LED's 29a, 29b provide an indication of particle counts and operational status respectively.

Screws 26 are used to mount the external housing to the counter 20. Those skilled in the art will recognize that no effort has been made to correlate each and every screw 26 to those illustrated in FIG. 1. Further, those skilled in the art will recognize that any other number of other suitable fastening means may be used.

B. Formation of the Light Sheet

Figure 12:
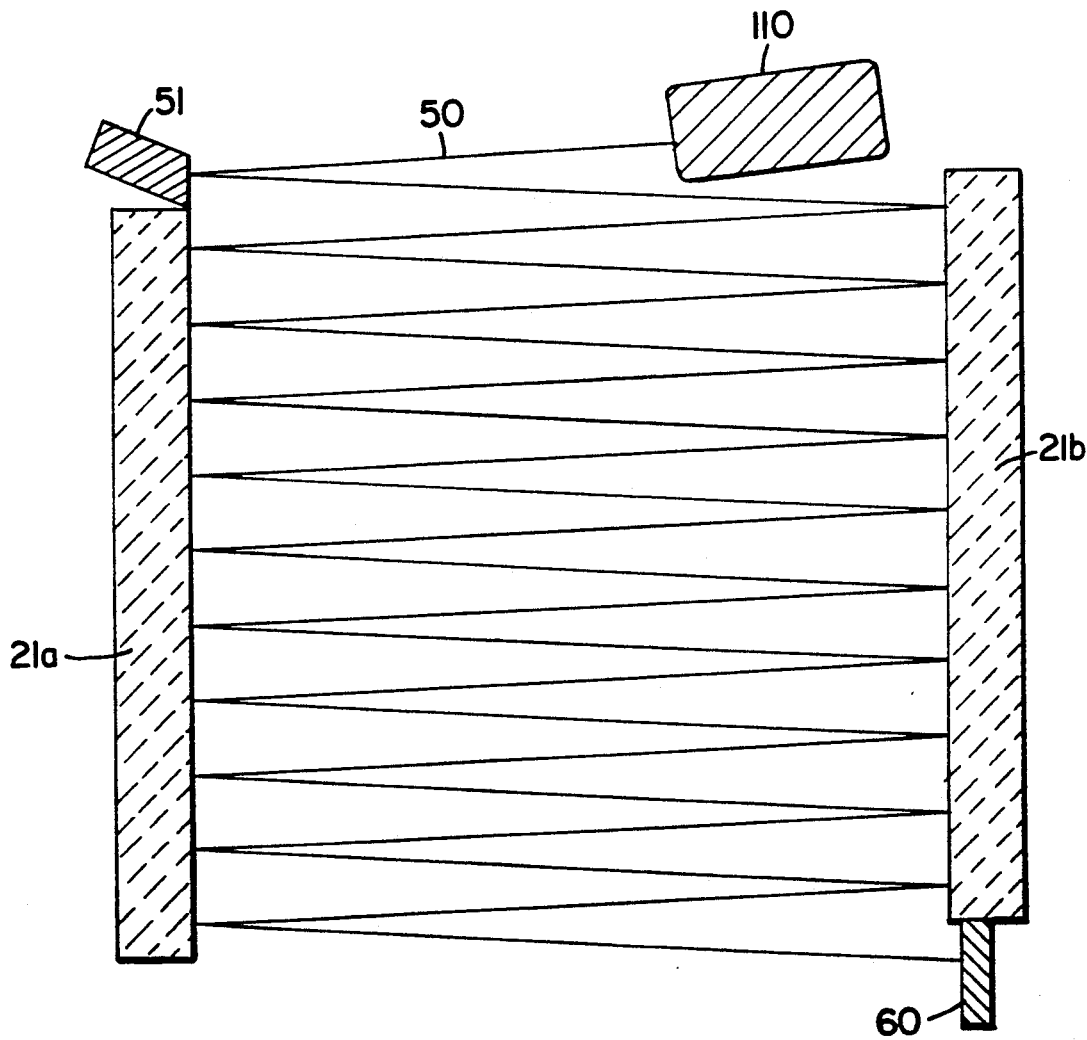
FIG. 12 is an alternative embodiment of a particle flux counter of FIG. 1.

In order to provide full coverage of the ESV 23, the laser beam 50 must cover every point within the ESV 23 at least once. There are several methods in which this can be achieved. First, as illustrated in FIG. 12, the beam 50 might be propagated through the ESV 23 by reflecting back and forth between the two cylindrical mirrors 21a, 21b and be monitored by detector means 60 at the longitudinal end of one of the cylindrical mirrors 21. This arrangement, however, requires a beam source 110 on one end of the system and a means for detection 60 on the other end, forcing the flow volume (monitoring cavity) to the middle of the device. Therefore, while described as an alternative embodiment, the configuration illustrated in FIG. 12 (described further below) is not the preferred arrangement due to applications which require the counter 20 to monitor sample aerosols next to machinery and the like. Additionally, the configuration illustrated in FIG. 12, although providing for one-hundred percent coverage of the sampling area, does not provide for overlapping the beam 50, thereby requiring much stricter tolerances to achieve such coverage.

In order to provide for a sampling capability of taking measurements essentially next to machinery and the like, the preferred apparatus and method allows the beam 50 to propagate through the sensing volume 80, leaving gaps between the beam reflections. The beam 50 then strikes a highly reflective flat mirror 22 which reflects the beam 50 back through the sensing volume 80 (best seen in FIG. 3d).

The beam 50 propagates back through the sensing volume 80 in the reverse direction, leaving the sensing volume 80 at the end in which the beam 50 was initially injected, but on the opposite side. This provides for the detection means 60 to be on the same side as the laser means 110 and beam shaping optics 40 (best seen in FIG. 2). Also, as the beam 50 propagates back through the system it fills in the gaps initially left as described further below in connection with FIGS. 3a and 3b.

Although the terms down and up are used in connection with describing the propagation of beam 50 as it forms a light sheet in ESV 23, those skilled in the art will recognize that such terms are merely terms of convenience to describe the incremental stepping of the reflections of beam 50 along the longitudinal length of cylindrical mirrors 21a, 21b. Further, those skilled in the art will recognize that sensing volume 80 is that area bounded by cylindrical mirrors 21, flat mirror 22 and a plane projecting between the ends of cylindrical mirrors 21 at the end opposite flat mirror 22. ESV 23 is that area within sensing volume 80 which is bounded by overlapping edges 24. The overlapping edges 24 are comprised of the edges of sides 25 of counter 20.

Referring next to FIGS. 3a, 3b, 3c, and 3d there is illustrated the ESV 23, of the counter 20. In counter 20 the ESV 23 is the active monitoring area of the apparatus. However, any single large particle intersecting beam 50, despite its position in the beam's 50 propagation path, will be detected.

Figure 3A:
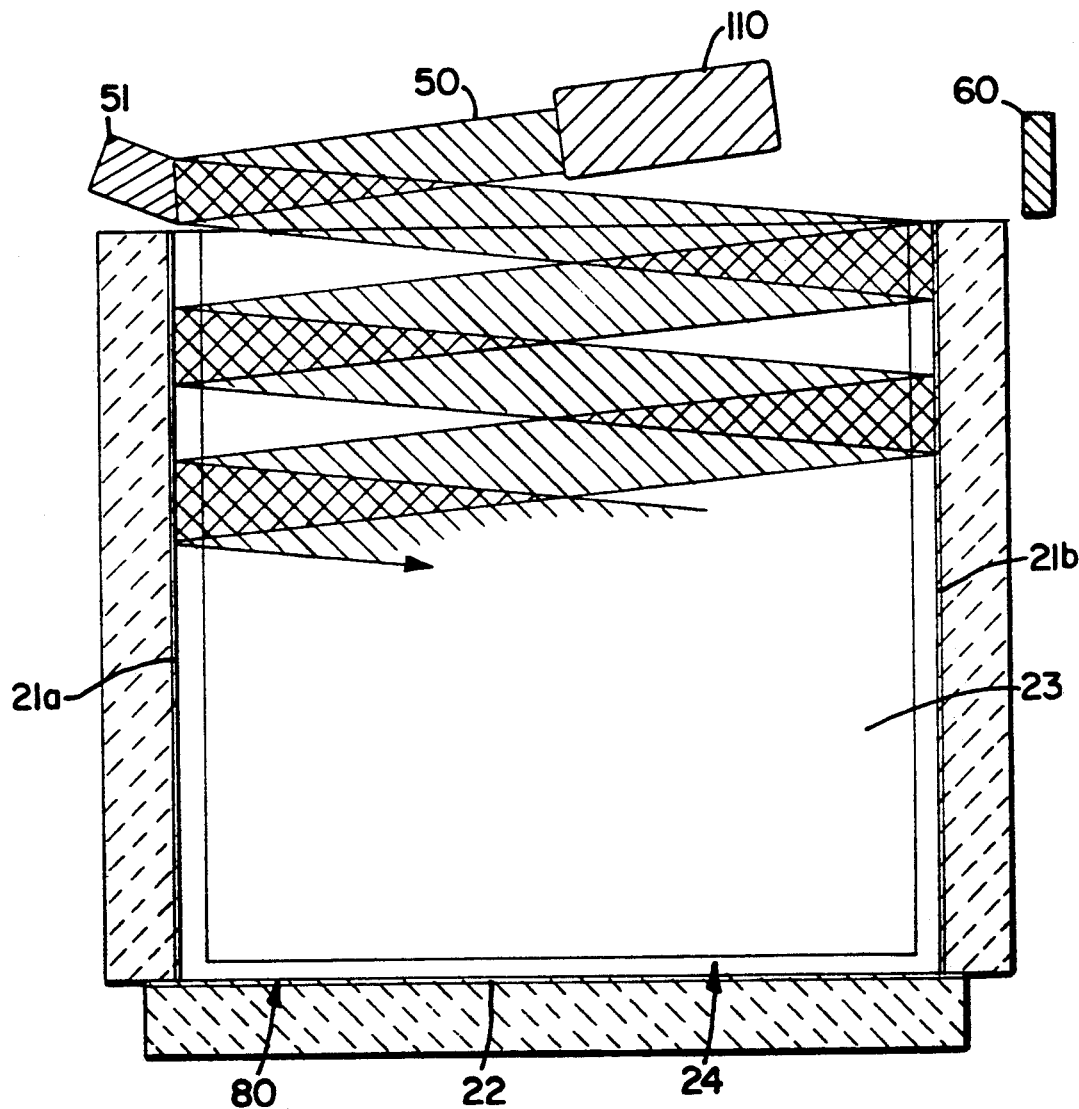
FIG. 3a is an unscaled diagrammatic illustration of the optical elements and a portion of the beam path traveling down the longitudinal length in first incremental steps through the sensing volume of the counter of FIG. 1.

As illustrated in FIG. 3a, laser beam forming means 110 generates a beam 50 which is directed by a steering mirror 51 into the sensing volume 80. The beam reflects back and forth between cylindrical mirrors 21a and cylindrical mirror 21b a predetermined number of times striking the mirrors 21 at a predetermined angle of incidence. Therefore, the beam 50 travels down the longitudinal length of the cylindrical mirrors 21a, 21b in first incremental steps.

Figure 3B:
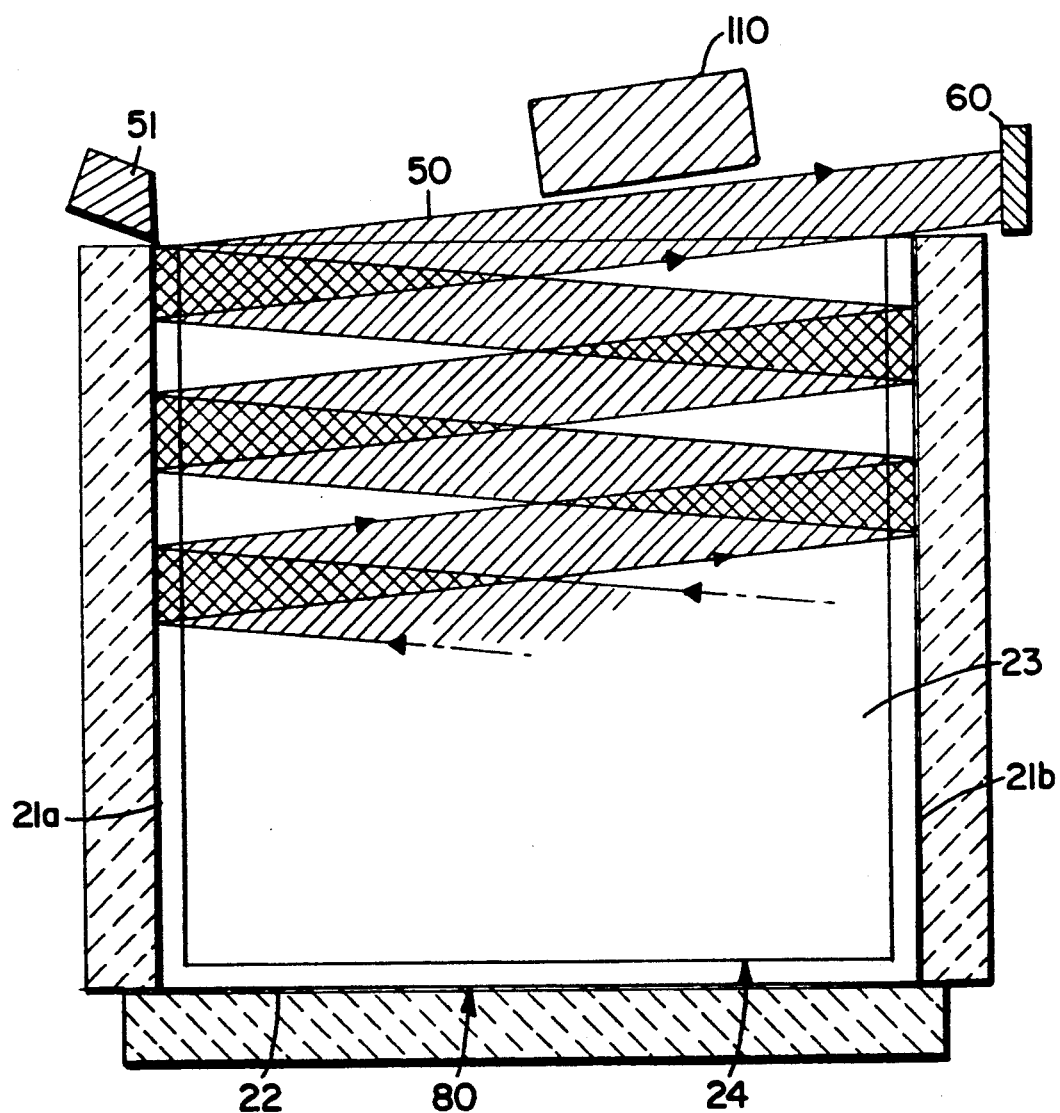
FIG. 3b is an unscaled diagrammatic illustration of the optical elements and a portion of the beam path traveling up the longitudinal length in second incremental steps through the sensing volume of the counter of FIG. 1.
Figure 3C:
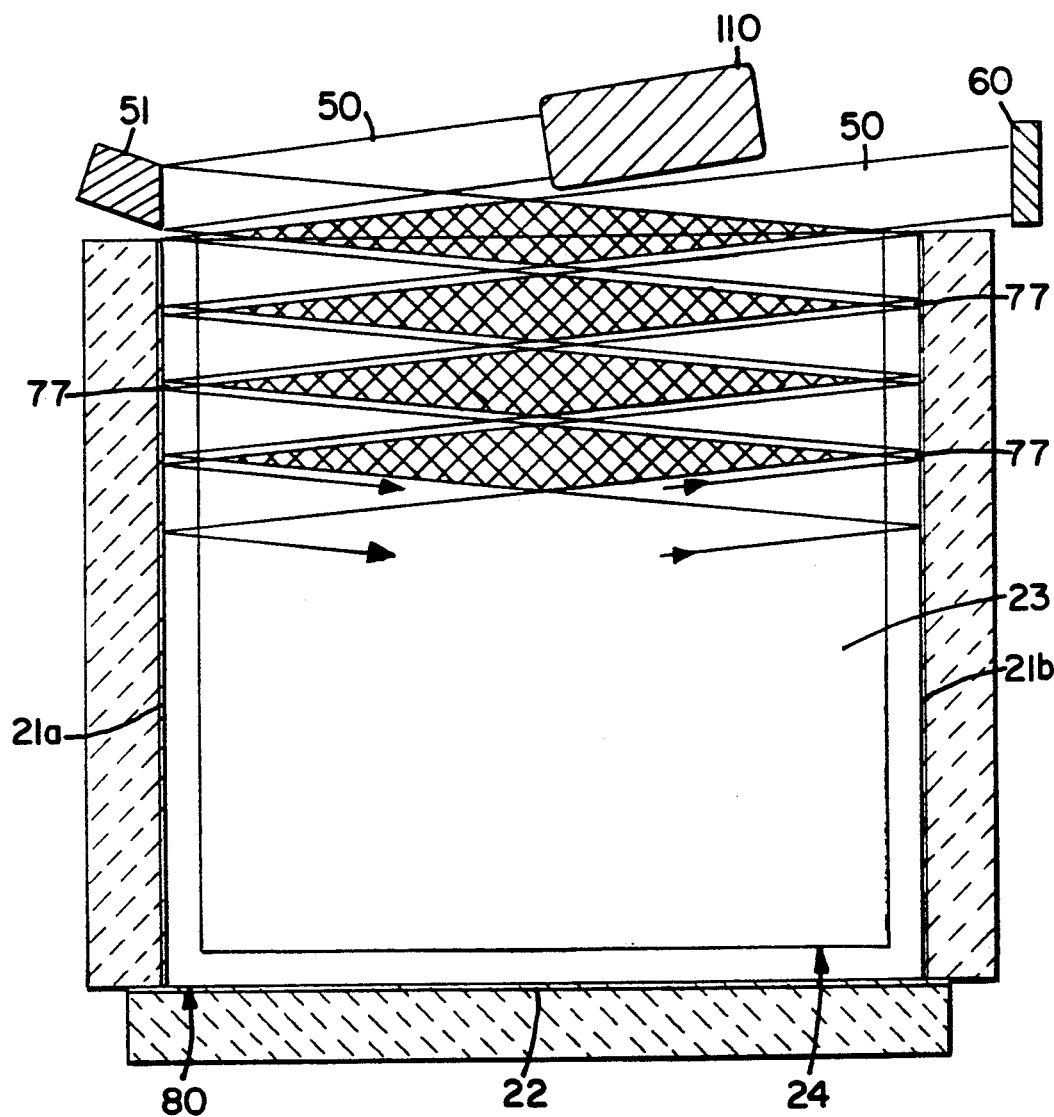
FIG. 3c is an unscaled diagrammatic illustration of the optical elements and resulting portion of the beam path of FIGS. 3a and 3b.
Figure 3E:
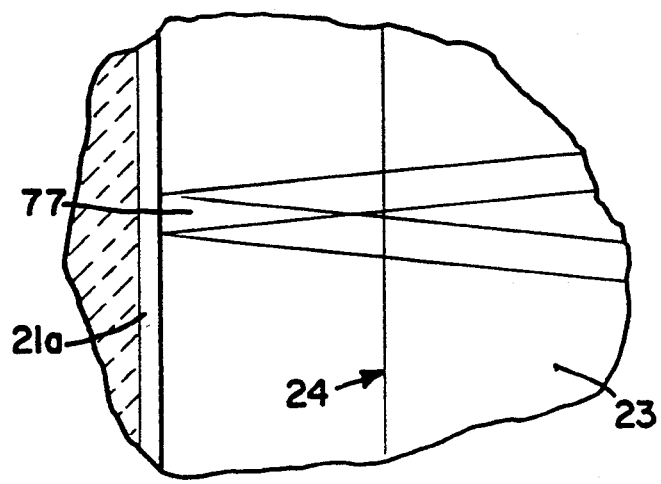
FIG. 3e is an enlarged portion of FIG. 3c illustrating triangular region 77.
Figure 3D:
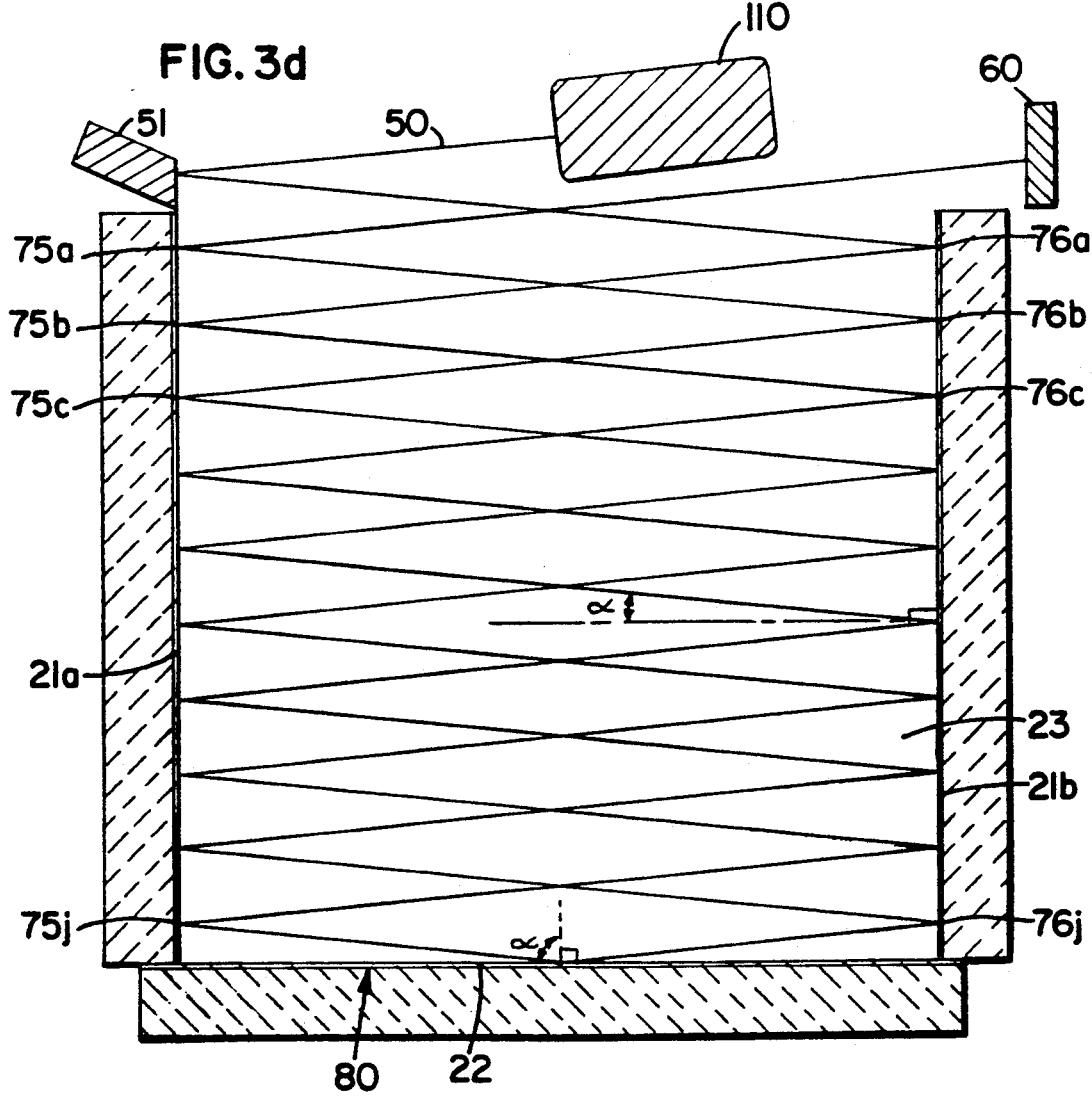
FIG. 3d is an unscaled diagrammatic illustration of the optical elements and the path of the beam through the sensing volume of the counter of FIG. 1.

Upon traversing the longitudinal length of the cylindrical mirrors 21, the beam 50 reflects from cylindrical mirror 21a onto flat mirror 22 (best seen in FIG. 3d). The beam 50 reflects off of flat mirror 22 back into the sensing volume 80. The angle of incidence of such reflection from flat mirror 22 is approximately 84° degrees, relative to the normal to flat mirror 22. Those skilled in the art will appreciate that areas 7 which are not "covered" by beam 50 are not within ESV 23 since areas 77 lie within the void formed by overlapping edges 24. Those skilled in the art will also recognize that the size of areas 77 may be properly adjusted so as not to reside within ESV 23 by the location of flat mirror 22 and the angle of incidence utilized, among other design consideration.

Next, as illustrated in FIG. 3b, subsequent to reflecting off of flat mirror 22, the beam 50 again travels along the longitudinal length of cylindrical mirrors 21, but in the opposite direction than in which the beam 50 originally traveled. In this second pass, the beam 50 travels in second incremental steps which interleave with the first incremental steps thereby forming a seamless sheet of light within the ESV 23. Upon traversing the entire longitudinal length of the cylindrical mirrors 21 for the second time, the beam 50 is reflected out of the sensing volume 80 onto detector means 60.

Figure 9A:
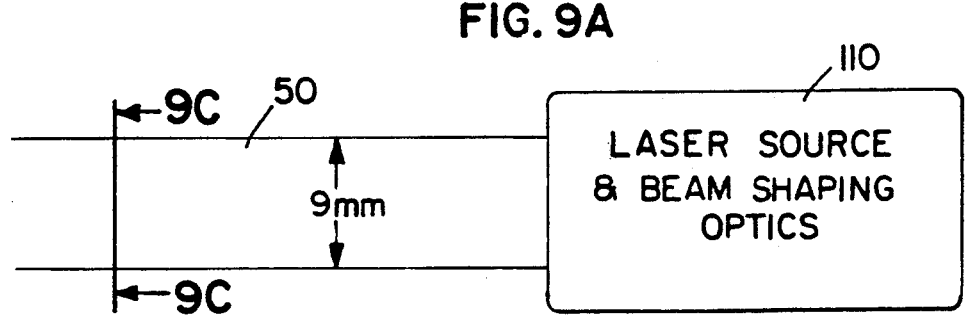
FIG. 9a is a top plan view of a portion of beam 50.

Referring next to FIGS. 3d and 9a, in the preferred embodiment, the beam 50 is nine millimeters in width. A twenty millimeter distance is utilized between the points at which beam 50 center to beam 50 center on consecutive reflections on the same cylindrical mirror 21 occurs. Therefore, from reflection 75a to reflection 75c the beam travels 20 millimeters down the longitudinal length of cylindrical mirror 21a. Between reflections 75a and 75c, beam 50 reflects off of cylindrical mirror 21b at reflection 76b. Those skilled in the art will recognize that the center point of reflection 76b projected back onto cylindrical mirror 21a is therefore at ten millimeters (center-to-center) from reflections 75a and 75c (the center point corresponds to reflection 75b). In the preferred embodiment the approximate angle of incidence $\alpha$ of beam 50, with respect to cylindrical mirrors 21a, 21b is 5.7° (degrees).

The shaded lines in FIG. 3a represent area covered by the beam 50. The cross hatched area indicates that portion of the sensing volume 80 in which the beam 50 overlaps upon itself when reflecting off of cylindrical mirrors 21.

Turning next to FIG. 3b, the beam is illustrated reflecting back up the longitudinal axis of cylindrical mirrors 21. The beam 50 cross-sectional width and the distance between consecutive reflections on each of the respective cylindrical mirrors 21a, 21b is similar to that described in connection with FIG. 3a. Cross hatching illustrates the beam 50 reflecting back upon itself, while diagonal lines indicate portions covered by the beam 50.

FIG. 3c illustrates those portions of the sensing volume 80 wherein the first (illustrated in FIG. 3a) and second (illustrated in FIG. 3b) beam passes overlap one another, as well as those triangular portions 77 of the sensing volume 80 which are not covered by the beam 50. As noted above, the portions not covered by the beam 50 are triangular portions 77, which are located within the recessed portion of side edges 25. Since triangular portions 77 are located within recessed areas (best seen in FIG. 3e), they are not within ESV 23 and so do not affect the sensing of particles.

Those skilled in the art will realize that although beam widths, incremental step distances, and the number of reflections are provided herein in describing the preferred embodiment counter 20, such measurements and parameters are a matter of design choice and the invention herein is not to be so limited. Further, those skilled in the art will recognize that although the preferred width of the beam 50 and the incremental step distance creates triangle portions 77 which are not covered by the beam 50, the beam width and/or incremental step distance may be adjusted to eliminate the triangular areas 77 thereby providing complete coverage of the entire sensing volume 80 of the device if so desired or required, and/or the size of the system might be changed.

C. Utilization of Light Extinction

Figure 2:
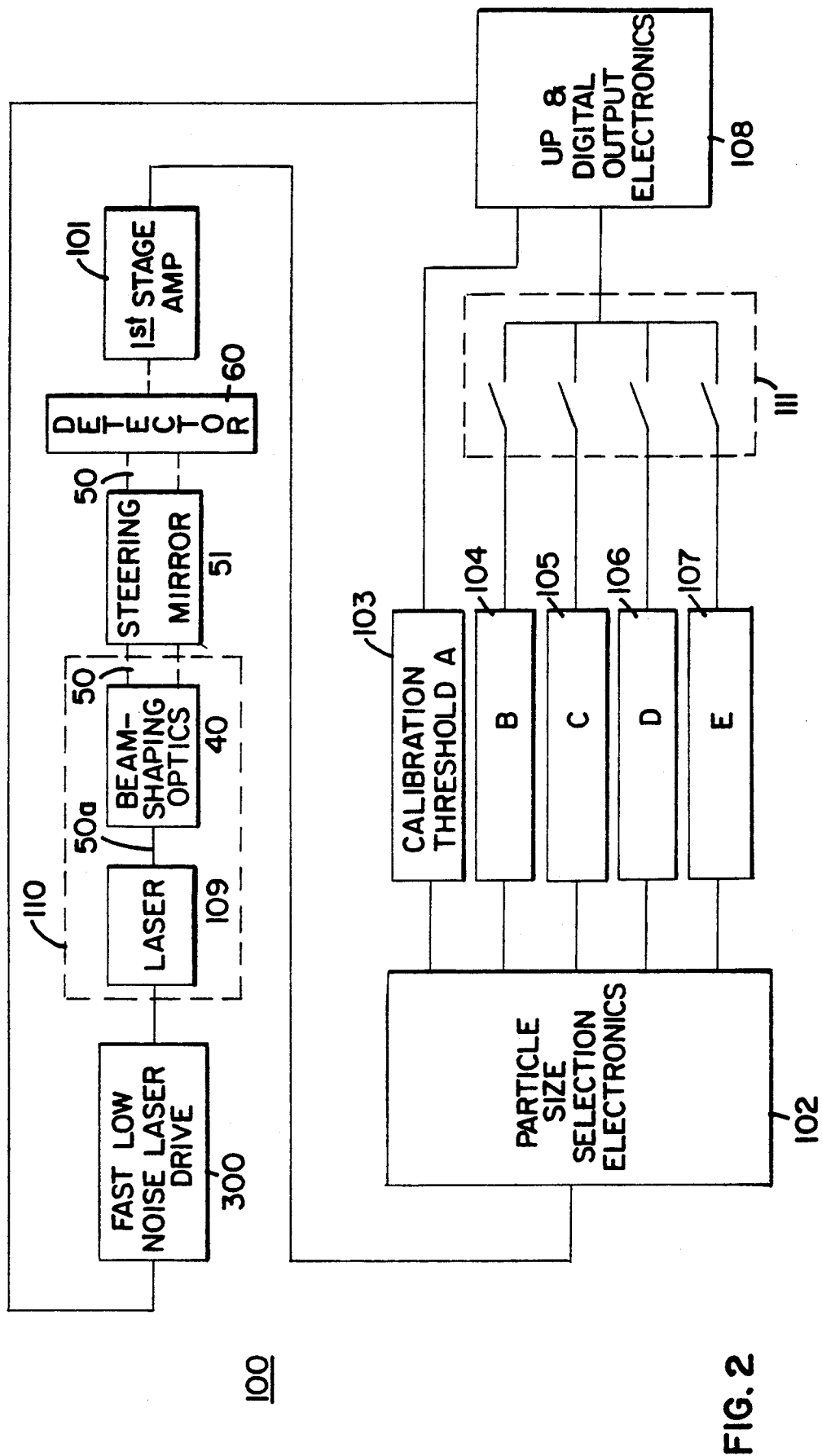
FIG. 2 is a block diagram illustrating functional elements of the electronics, and portions of the optical elements, of a preferred embodiment counter of FIG. 1.

To facilitate understanding of the counter 20, the description of the functional blocks of FIG. 2 and the beam generating, shaping and refocusing will now be deferred pending a discussion of light extinction and its use in apparatus 20.

Light may undergo multiple interactions when it encounters a particle. The five major interactions of particles and light are as follows: (1) Diffraction, when photons of light pass by the particle and are bent toward or away from it; (2) refraction, when photons pass through the particle and their path is changed because of the different indices of refraction of the two media; (3) reflection, when photons hit the particle and are reflected away; (4) absorption, when photons hit the particle and are absorbed into it, transforming their energy into heat; and (5) thermal emission, when particles cool and emit photons. For a more thorough discussion of such light interactions see, for example, Bohren and Huffman, *Absorption and Scattering of Light by Small Particles* (1983).

Counter 20 utilizes light extinction principles in order to provide more accurate particle sensing. FIG. 4 illustrates a particle intersection with beam 50 and the resulting light extinction. The particle is illustrated at 90 having traveled along the direction indicated by the arrow. The particle 90 intersects beam 50 at point 91 which comprises an intersection volume. The sum of all possible intersection volumes 91 in counter 20 comprise the ESV 23 (i.e., since those areas of the beam 50 within the recessed edge 24 also may provide an intersection volume, the sum of all possible intersection volumes equals the sensing volume 80 of counter 20).

FIG. 4 further illustrates a reduction in light intensity 92 striking the detector means 60 as the particle 90 intersects the beam 50. In FIG. 4, the particle 90 has been illustrated in a physical position which is not within the beam 50 although the light intensity path decrease 92 is still occurring. Those skilled in the art will realize that the light intensity decrease path 92 will occur approximately instantaneously with the intersection of particle 90 with beam 50, due to the relative speeds of the particle 90 and light which comprises beam 50. This will hold true no matter which intersection volume 91 within ESV 23 is chosen, due to the magnitude of the speed of light. Those skilled in the art will recognize that the signal received by detector means 60 must therefore be designed to detect signals dependent upon the velocity of particle(s) 90 intersecting ESV 23.

Light extinction itself may be defined by the following equation:

$$C(ext) = C(sca) + C(abs); \qquad (1)$$

where C(ext) is extinction, C(sca) is scattered, and C(abs) is absorbed. The principles of light extinction are well known to those skilled in the art and so will not be further described herein. However, A more detailed discussion may be found, in H.C. van de Hulst, *Light Scattering By Small Particles* (1981).

The scattered light portion of equation (1) may be defined as follows:

$$C(sca) = 1/k^2 \int F(\phi\theta) dw; \qquad (2)$$

where K equals $2\pi/\lambda$, a constant to adjust for wavelength dependencies and $$dw = \sin(\phi) \, d\phi d\theta. \qquad (3)$$

From the foregoing, one can easily see that the scattering integral of equation (2) is calculated over some $d(\phi)$ and $d(\theta)$ angular range (wherein $\phi$ and $\theta$ are polar coordinates). As $d(\phi)$ and $d(\theta)$ approach zero, it can be shown that the scattered light approaches zero for that area.

In the present invention, $d(\phi)$ and $d(\theta)$ are the angular representations of the counter 20 position with respect to the coaxial x-y-z beam plane, where the origin is defined as the point at which the particle intersects the beam (i.e. a cartesian coordinate system may be defined by the longitudinal path of beam 50 defining the x-axis, the beam width defining the y-axis and the normal to the plane formed by the x and y axis defining the z-axis).

In the preferred embodiment, the counter 20 works especially well in connection with large particles (i.e., these particles which are 10 $\mu$m and larger). The geometric light scattering approximation for large particles treats the particle as a lens and does ray tracing through the particle. This may be performed to calculate refracted light (see A. Ungut, G. Grehan and G. Gouesbet, *Comparisons between geometric optics and Lorenz-Mie theory* Applied Optics. Vol. 20, 2911, 1981). The light interfered with by the particle is considered in three basic areas: absorption, reflection and refraction. The absorption does not need to be calculated since the light absorbed is extracted from the signal and thereby adds directly to the extinction signal. The reflected light is reflected symmetrically about the particle and the amount reaching the detector can be considered proportionally to the detector solid angle as compared to the $4\pi$ scattering volume. This percentage of reflected light that reaches the detector must be subtracted from the extinction signal since it cancels out some of the extinction effect. As noted, refraction may be accomplished by ray tracing and using the particle as a spherical lens element having a finite focal length and conical output wave front. The area of the conical front is then compared to the overlapping area of the detector. If the refracted light does not reach the detector, it can be added directly into the extinction result.

Those skilled in the art will recognize that by taking random particle positions in the ESV 23 of the preferred embodiment counter 20 and calculating the amount of scattered light reaching the detector means 60 of the present invention, as a function of the total light interfered with, it can be shown that the scattered light received by the detector means 60 is of such a limited contribution that it may be ignored. Therefore, equation (1) is verified as the model equation for a counter 20 constructed according to the principles of the present invention.

Figure 7:
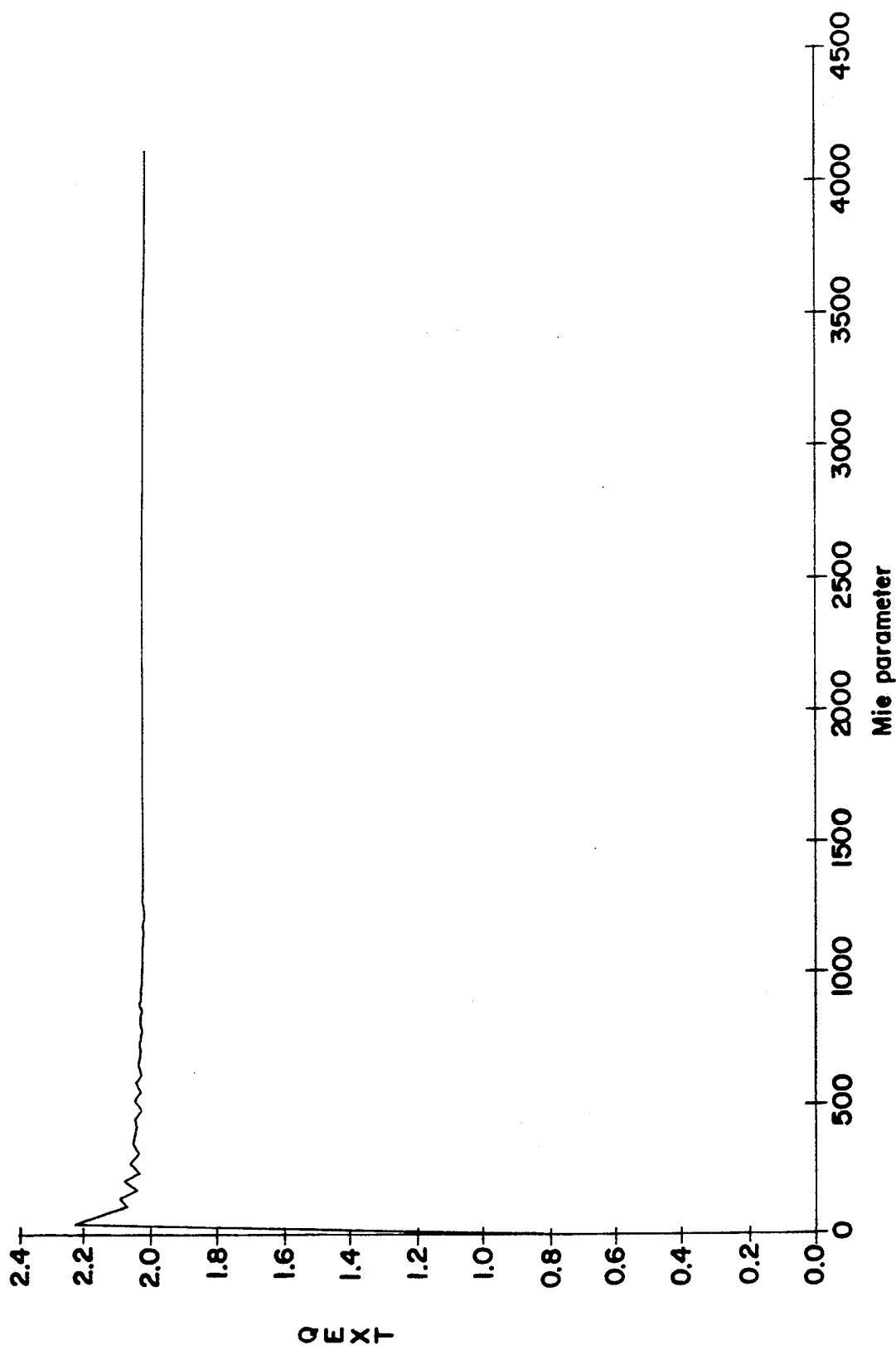
FIG. 7 is a graph depicting the correlation between particle size and light extinction.

Therefore, in summary, in the preferred embodiment counter 20, particles interfere with the light sheet by absorbing a portion of the light incident on the particle and reflecting or refracting a portion of light out of the beam path. The detector means 60 monitors the received light intensity from the beam path. When no particle is intersecting the beam path (i.e., no particle is within the ESV 23), then the intensity is greater than when a particle intersects the ESV 23. Therefore, the present invention operates utilizing light extinction principles. Such operation provides excellent linear operating characteristics, although a limited nonlinearity does occur at the lower particle size counting limits of the counter 20. FIG. 7 illustrates the operating linearities of counter 20.

FIG. 7 also illustrates the proportionality between signal magnitude and particle size, wherein $Cext = (\pi a^2)(Qext)$. The proportionality occurs for large particles in which the wavelength of light is much less then the diameter of the particle. The relationship is known as the paradox of extinction. This paradox predicts that the amount of light extinction by a particle will be approximately equal to two times the particle's geometric area, thereby allowing for a device where the signal is almost directly proportional to particle size. Light scattering particle detection devices, on the other hand, do not exhibit such a linear relationship due to the angular dependencies of scattered light.

D. Beam Generation, Shaping and Refocusing

Figure 9B:
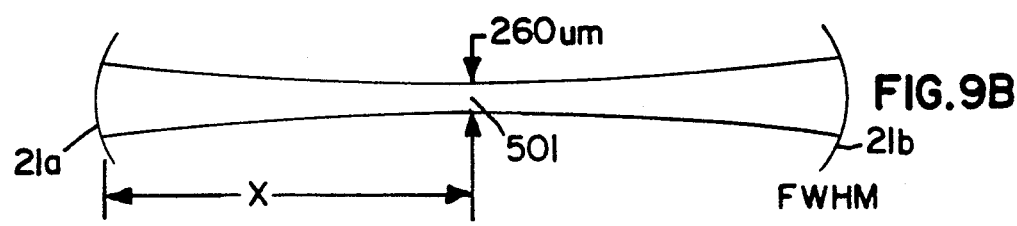
FIG. 9b is a side view of a portion of the beam 50.
Figure 9C:
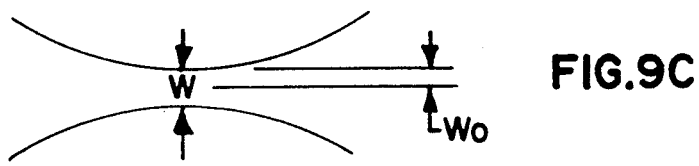

Returning now to the preferred embodiment counter 20 and FIGS. 2, 5, and 9, a means for generating a wide flat beam 50 in order to form a sheet of light is required. Beam shaping optics 40 act upon the generated beam first. Beam shaping optics 40 are comprised of a collimating lens (not shown), a Galilean telescopic arrangement (not shown) and cylindrical optics (not shown). The output laser light of the P-N junction of the laser 110 is first collimated by well know collimating lens techniques. A pencil shaped beam is produced. This beam is then run through a Galilean telescopic arrangement which offsets the axis of the beam and expands its width. This is followed by a set of cylindrical optics which thin and focus the beam to a finite waist at some predetermined point. This is important because a thin flat beam of light is needed to create the light sheet in the ESV 23. The width allows for a large area to be covered and the height of the beam is kept to a minimum to keep the laser power density at a maximum. The Galilean telescopic beam expansion system with prisms is used because of their efficiency, cost and axis offset. This offsetting of the axis allows the beam shaping optical assembly to be mounted closer to the ESV 23 without interfering with the beam 50 as it exits the ESV 23 onto the detector means 60. This in turn allows for a more efficient and smaller counter 20 to be designed.

The beam 50 preferably has a waist 501 of 260 μm (H) at the full width half max power points (FWHM). This waist 501 falls at distance x from the beam shaping optics (best seen in FIG. 9b). Preferably distance x is approximately at the half way point between cylindrical mirrors 21. In the preferred embodiment, distance x is 80 mm (i.e., where x equals the distance from the beam shaping optics 40 to the steering mirror 51 and then into the center of the ESV 23). From this point on, the waist is reconverged into the center of the system as depicted in FIG. 9b.

The width (W) of the beam 50 at the first waist is preferably 9mm and the diffraction is limited so as not to diverge out of the counter 20. To keep the beam 50 from diverging out of the counter 20 in the z axis direction, cylindrical mirrors 21a, 21b are used to refocus the beam 50 upon each reflection 75, 76. These mirrors 21a, 21b are designed such that the Gausian beam profile is refocused to a waist 501 at the center of the ESV 23 every reflection 75, 76.

Therefore, if:

$$W_o = W/2, \quad (4)$$

$$Z = \text{distance from waist, and} \quad (5)$$

$$Z(r) = [\pi * W_o^2]/\lambda \quad (6)$$

Then the ratios of curvature of cylindrical mirrors 21 may be calculated as follows:

$$R = [Z(r)^2 + Z^2]/Z. \quad (7)$$

By using formula (7) and the given parameters, the cylindrical mirrors 21a, 21b can be designed in the preferred embodiment with ratios of curvature equal to 0.1427 meters. This forces the waist 501 of the beam 50 to be Gausian in nature and converge to the center of the ESV 23 during its propagation path. This insures a high power density throughout the entire ESV 23 and thus insures better signal to noise.

Subsequent to beam shaping optics 40, the beam 50 is deflected off of steering mirror 51. Steering mirror 51 is comprised of a center ball bearing surrounded by three screws in a triangular arrangement. This allows for a slight angular redirection of the beam exiting beam generating means 110 before it enters ESV 23. This is done to relax the tolerances of the beam generating means 110. Those skilled in the art will recognize that other beam directing devices, such as prisms, gratings, etc., might also be used.

After steering mirror 51, the beam 50 is then propagated through the sensing volume 80 between the two cylindrical mirrors 21a, 21b. These mirrors 21 must have a high reflectively due to the number of times the beam 50 bounces between them. The total efficiency of the propagation path is the individual efficiency to the power of the number of bounces (i.e., $EFF = x^y$ wherein x is the reflectivity and y is the number of bounces). In the preferred embodiment a thin film multilayer dielectric coating (not shown) is used. This coating is comprised of multiple layers of thin films with different indices of refraction and is 99.8% efficient at near normal incident for light having a 780 nm wavelength.

As noted above, the preferred embodiment utilizes 20 reflections on each cylindrical mirror 21a, 21b surfaces therefore, the resulting efficiency is 96.1% ($99.8^{20} = 96.1\%$). A protected enhanced silver plating could also be used, as those skilled in the art will realize, however, the reflectively of such a plating is only 98.9% and the system efficiency would then be lowered to 80%. Further, such a power change would cause a nonlinearity in the counter's 20 sizing capability due to its dependencies on power.

E. Functional Blocks of Counter 20

Turning next to FIG. 2, there is illustrated a block diagram illustrating functional elements of the counter 20 electronics 100. The fast low-noise laser drive 300 is connected to laser 109 which generates a beam 50a. The beam 50a is directed through beam shaping optics 40, forming beam 50, and onto steering mirror 51. The beam 50 propagates through the sensing volume 80 and strikes detector means 60. Connected to the output of detector means 60 is a first stage amplifier 101, whose output is connected to the particle size selection electronics 102 (PSSE). Connected to the output of PSSE 102 are calibration threshold blocks a, b, c, d and e 103-107 respectively which are connected to the microprocessor and digital output electronics device 108 via DIP switch 111.

In operation, detector means 60 receives the laser beam 50 and monitors power changes in order to detect particles. The intersection of a particle with the beam 50 causes an impulse in the power intensity of the beam 50. The amplitude of the pulse is proportional to the size of the particle and the duration of the pulse is proportional to the velocity of the particle. First stage amplifier 101 amplifies the signal received from the detector 60. First stage amplifier 101 is preferably placed on or near the detector 60 to reduce noise. Additionally, amplifier 101 is preferably a low noise op amp. PSSE 102 receives the amplified signal from first stage amplifier 101 and provides active Bessel filtering to set the bandwidth of the system. PSSE 102 also separates the a.c. pulse signal to different gain stages for different particle viewing ranges; with high gain required for small particles and low gain for large particles. In essence, gain is used to compensate for different size particles. Therefore, dependent upon the size of particles being encountered and sampled, various calibration threshold blocks 103-107 are provided.

Calibration threshold block A 103 provides a small channel threshold. Calibration thresholds 104 through calibration threshold E 107 provides selectively larger channel viewing. These calibration thresholds B-E 103-107 are set during initial calibration of the counter 20. Particles are passed through the counter 20 as the threshold is set at the average peak voltage.

Preferably, threshold block A is connected to microprocessor 108 and one of remaining threshold blocks B-E 104-107 are connected to microprocessor 108 through switch DIP switch 111. In the preferred embodiment threshold blocks B-E are comparators with individually adjustable thresholds.

Microprocessor and digital output electronics 108 receives the small and large input signals from calibration threshold A 103 and one of calibration thresholds B-E 104-107 and converts it to a digital signal for other devices (not shown).

While not specifically detailed, it will be understood by those skilled in the art that the various functional elements are to be properly connected to appropriate bias and reference supplies so as to operate in their intended manner. Similarly, it will be understood that appropriate memory, buffer and other peripheral devices are to be properly connected to microprocessor 108 and other functional elements so as to operate in their intended manner.

F. Detector Means 60

Figure 10:
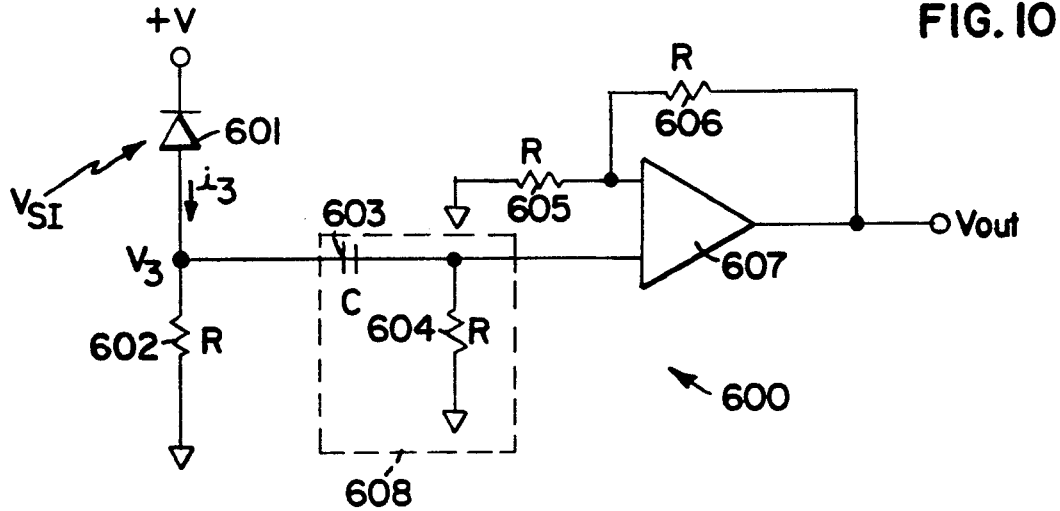
FIG. 10 is a schematic diagram of a preferred circuit configuration of blocks 60 and 101 of FIG. 2.

Referring next to FIG. 10, there is illustrated a preferred schematic for the electronics portion 600 of detector means 60. Detector means 60 is comprised of electronics portion 600, filter 650, and aperture 660.

Referring first to electronics portion 600, the voltage source $+V$ is connected to the cathode of photosensitive diode 601. The anode of photosensitive diode 601 is connected to resistor 602 which is tied to ground. The anode of photosensitive diode 601 is also connected to capacitor 603 which is in turn connected to resistor 604 and Op amp 607. The inverting input of Op amp 607 is connected to resistor 605 to ground and to gain resistor 606, as well as signal output Vout.

In operation, photosensitive diode 601 is made conducting when counter 20 is in operation (i.e., diode 601 is normally in the path of beam 50). Resistor 602 establishes a dc voltage level $V^1$ while capacitor 603 and resistor 604 act as a high pass filter 608. Therefore, when no particles are intersecting the ESV 23, voltage drop $V^1$ is across capacitor 603 and Vout is equal to zero (0) volts. When a particle intersects ESV 23, voltage $V^1$ will include an ac component which is transmitted to Op amp 607 through high pass filter 608. The detector means 60 provides Vout to the particle size selection electronics 102.

Op amp 607 is a low voltage noise, high gain op amp, within the bandwidth of the counter electronics 100. In order to insure that the signal to noise of the counter 20 is maximized, the particle signal in (Vsi) must be greater than the current shot noise of photodiode 601 and also greater than the Op amp voltage noise of op amp 607.

Figure 8A:
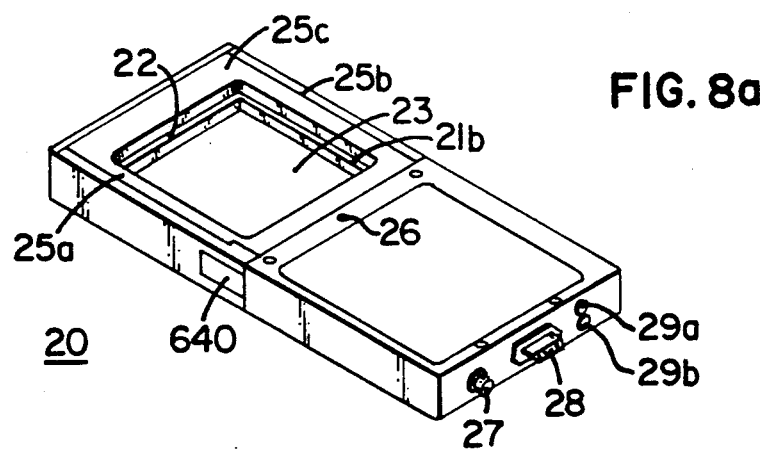
FIG. 8a is the particle flux counter of FIG. 1 from a second perspective view.
Figure 8B:
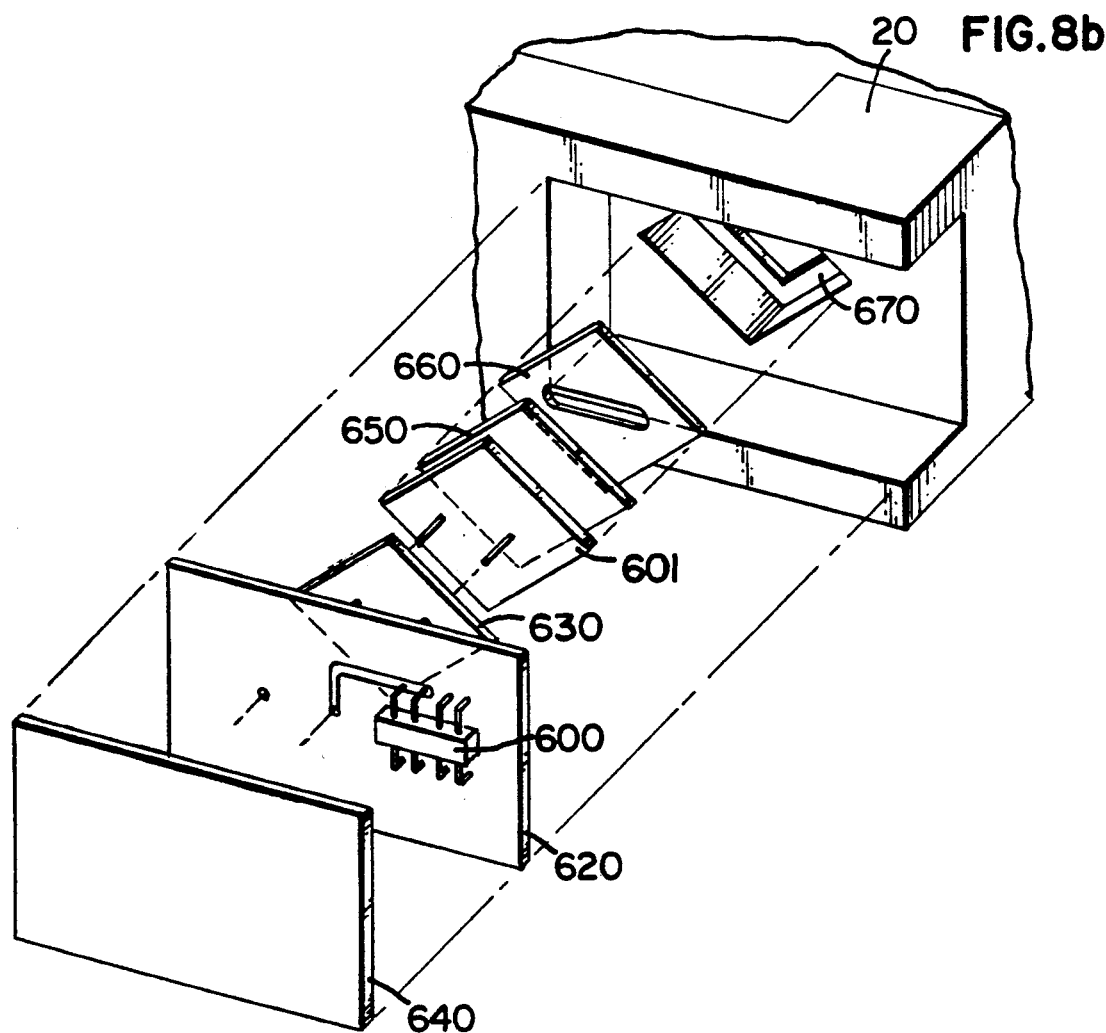

Referring next to FIG. 8a, there is illustrated a perspective view of counter 20 illustrating the location of side panel 640. FIG. 8b illustrates an exploded view of the detector means 60 when side panel 640 is removed. Detector means 60 is comprised electronic portion 600 mounted on P.C. board 620, mounting cushion 630, photodetector 601, filter glass 650, and beam aperture plate 660. Each of the components fits sequentially into detector means cavity 670.

Beam aperture plate 660, provides for a plate having an aperture formed therethrough to allow the beam to pass undisturbed through the beam aperture plate 660, but cover the unused portion of the detector 601 to keep other light signals minimized. Located between photodetector 601 and beam aperture plate 660 is filter 650 which further reduces stray light by filtering out wavelength components and only allowing the wave length of beam 50 to pass through filter 650. Preferably, filter 650 is comprised of a thin film dielectric coating with a band pass of about 210 nm centered about the wavelength of beam 50, thereby allowing for the slight variances in laser wavelength outputs to pass. A dielectric filter also has a very sharp fall off to limit the input wavelength into the detector and keep out unwanted light signals.

Photodetector 601 is preferably a large area pin photodiode as are well known in the art. Detector 601 is mounted onto the printed circuit board 620 on which circuit 600 resides.

G. Laser Drive Electronics

Referring next to FIG. 6, if the electronics can be kept quieter than the shot noise of the detector means 60, the limiting factor of the counter 20 is set by the light intensity noise into the detector means electronics portion 600. Therefore, it is desirable to generate a "quiet" beam 50, or a beam with intensity irregularities at a frequency out of the detector means 60 detection limit. In such a situation, the system noise is the shot noise of the detector means 60 described by:

$$\text{Noise} = (2bei) exp \tfrac{1}{2} \quad (8)$$

where b is the bandwidth of the system, e is the electron charge, and i is the detector current. This allows for the preferred embodiment counter 20 to operate at its theoretical shot noise limit, and thus function with a larger signal to noise for a given particle size.

Currently there are lasers designed for low noise applications in which the output intensity is quite stable, one example being the laser manufactured by NEC corporation designated by model number Sharp LT023MF. However, these lasers cost more than standard lasers. The present invention provides for using a standard laser, an example being the Mitsubishi ML4412A, and controlling it in a fashion so as to maintain the noise frequency above the detection bandwidth limits.

The ML4412A laser operates at a 780 nm wave length. Since light extinction is inversely proportional to the square of the wavelength of the laser, those skilled in the art will recognize that a shorter wavelength laser might also be used.

The laser 109 itself has a function of energy output versus temperature, current and wavelength. When this band gap energy randomly changes, it causes a change in the output wavelength which in turn causes an intensity output change. As described above, the detector means 60 of the preferred embodiment monitors this light directly and looks for intensity changes. If this random intensity profile is not accounted for, the counter 20 will count these changes as a particle extincting light from the beam 50.

The preferred detection circuit has an upper bandwidth limit of 20k HZ. This is designed by establishing the maximum particle velocity expected to be encountered and the beam width w.

FIG. 6 illustrates a preferred circuit which maintains a constant intensity laser. A typical laser diode has two lasing facets. One outputs a light beam from the front of the diode package (laser beam output) and the other outputs a beam into the back of the laser diode package (laser monitor beam). Many manufacturers of laser diodes have installed a small silicon photodiode in the laser diode package to monitor this light intensity from the back laser facet. Currently available are constant power laser drive IC chips which monitor this feedback light and supply a drive current to the laser diode for a constant output power. The problem of these devices, however, is they are designed to allow for current changes occurring when the laser ages and are therefore quite slow. However, by using the preferred circuit illustrated in FIG. 6, an electrical laser drive circuit can be designed with dependencies upon the output power. These dependencies can be designed to have a certain frequency response and thus tailored to a system.

With a laser power control circuit of finite gain and bandwidth, the laser output power change will be monitored by the monitor detector 307. The laser intensity change causes a current change $i_1$ through the laser monitor circuit 300. The resistor-capacitor network 301 of the circuit converts this current into a voltage V1. Op amp 302 buffers voltage V1 and inputs it into the voltage dividing power control circuit 303. This voltage is then input to op amp 304 which inverts the change about the voltage reference V(r) and outputs the difference into transistor 305. Transistor 305 controls the laser drive current $i_2$ from laser diode 308.

Laser drive means 309 is comprised of transistor 305 and appropriate resistors. Feedback means 310 is comprised of first means for determining laser intensity 311 and second means for creating an error signal 312.

One example of operation of circuit 300 occurs when the laser mode changes. In this instance, the output power increases and the voltage $V_1$ into op amp 302 increases. Accordingly, the voltage into op amp 304 is then also increased. The output signal of op amp 304 then decreases. Finally, this decrease causes the current $i_2$ in the laser to decrease and its output power decreases.

Resistor-capacitor network 301 is used to set the maximum feedback frequency to ensure the system will not oscillate. This sets the limit at which output noise starts in the preferred embodiment 800kHz, which is above the bandwidth of particle detection (approximately 20kHz).

Figure 13A:
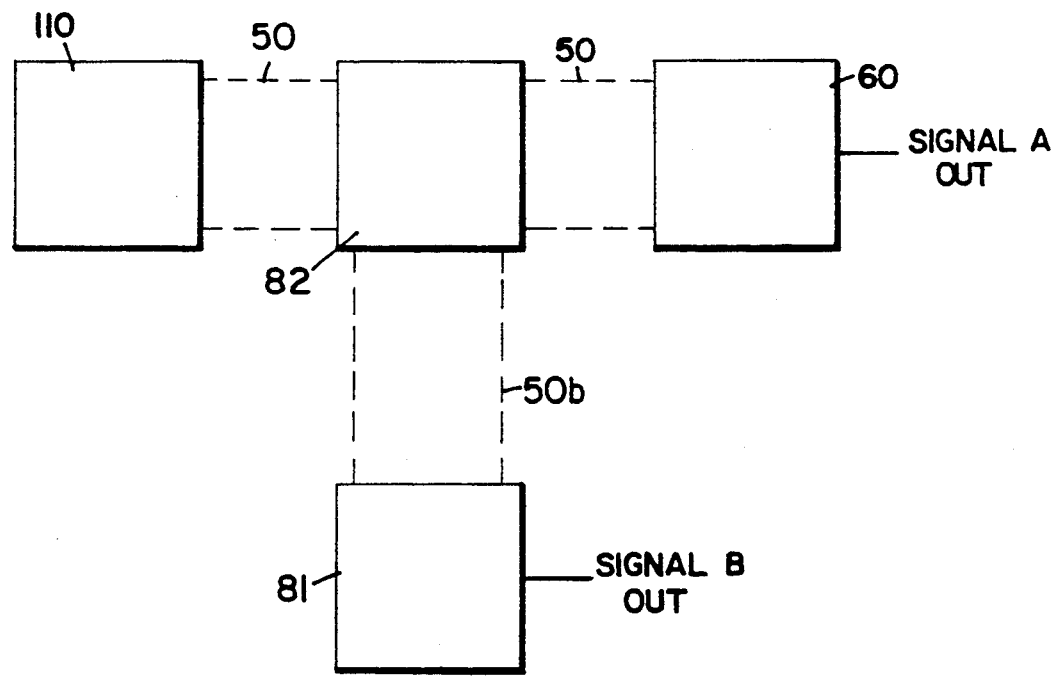
FIG. 13a is an alternative functional block diagram of an alternative method of compensating for beam 50 noise.
Figure 13B:
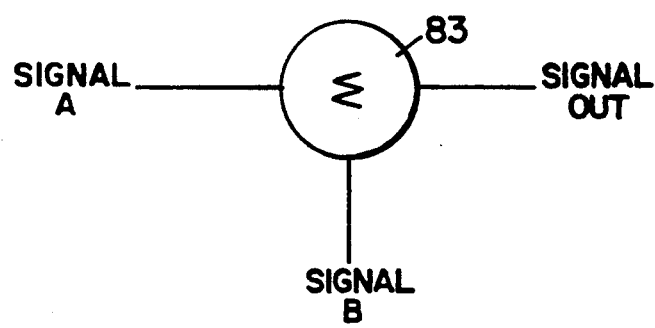

Referring next to FIGS. 13a and 13b, an alternative technique for reduction of noise in the apparatus 20 to achieve higher measurements sensitivity may also be utilized. This alternative technique operates utilizing the principle that the light emitted from diode lasers has noise characteristics that are higher than the theoretical quantum noise for the emitted light power. This excess noise appears in the electrical signal from the primary photodetector which senses the particle signals. The noise in the electrical signal which is processed to provide particle information can be reduced to nearly the quantum limit by using normal electronic means to produce a signal proportional to the electrical difference between the electrical output of the primary photodetector and the electrical output of a second photodetector which receives light from the laser before the laser beam enters the measuring cavity. For optimum noise reduction, the photocurrents of the two photodetectors should be of similar magnitudes. Alternatively expressed, a signal proportional to the excess laser noise before the beam enters the cavity is produced, and this excess noise is subtracted out of the signal from the particle signal photodetector, leaving a signal which contains only the particle signals and the quantum noise inherent in the photodetector signals. For lower cost and simplicity of design, this technique may use the photodetector included in the package of commercial diode lasers as this second photodetector. However, since this photodetector receives light through the laser facet opposite the facet through which the main beam emerges, its signal may contain some excess noise that is not perfectly correlated with the excess noise in the main beam.

Thus, another approach is to include a separate photodetector 81 which receives a second portion 50b of the main beam 50 before it enters the ESV 23. This may be accomplished through normal optical beam splitter 82 techniques, or by sensing a portion of the laser light that is reflected from lenses or prisms already used in the optical path. A summing device 83 then subtracts the noise signal (signal B) from the detector means 60 intensity signal (signal A).

H. Alternative Laser Pulsing Circuit

Another constraint and inherent problem of an extinction based particle detection device 20 where the laser beam 50 is directly incident on the detector means 60 is the power limitations of the system. The extinction signal is directly proportional to the power density of the light the particle passes through. The noise level is proportional to the square root of the power. So by doubling the power, the signal to noise only goes up by the square root of two. The limiting factor is the power density allowed into a standard silicon PIN photodetector comprising detector means 60. If a constant light intensity is applied to a pin photodiode (i.e., of the photodiode 601 type utilized in the preferred embodiment), it will go into thermal saturation at about 5 mw. Special, more expensive photodetectors have been designed to allow for higher power densities, but they cost more and still do not allow for large power densities. If the present method is to be utilized to detect small particles (e.g., 1 um) a laser beam of 100 mw or greater should be used. Currently this is not possible with standard PIN photodiodies. However, by modulating the laser diode to produce a fast repetition rate and low duty cycle, a large power laser may be utilized. This allows for a high peak power for small particle sensitivity and a low time averaged power so the photodetector will not go into thermal saturation.

This pulsing offers an additional side effect by producing a low noise laser. More specifically, when a laser is operated in the pulsed mode, the inherent noise problems of the constant power mode disappear. Also the band width of the system stays the same, but the frequency in which the system operates is raised so the 1/F noise is lowered. The final and most advantageous side effect of this modulation is that common mode noise disappears (i.e., vibration noise, room light noise and radio interference). By using this modulated mode of operation, a high power, low noise, common mode rejection system is all installed at once. Therefore eliminating interference filter glass to block out room light, and band pass filters to filter out the inherent vibration noise.

Figure 11:
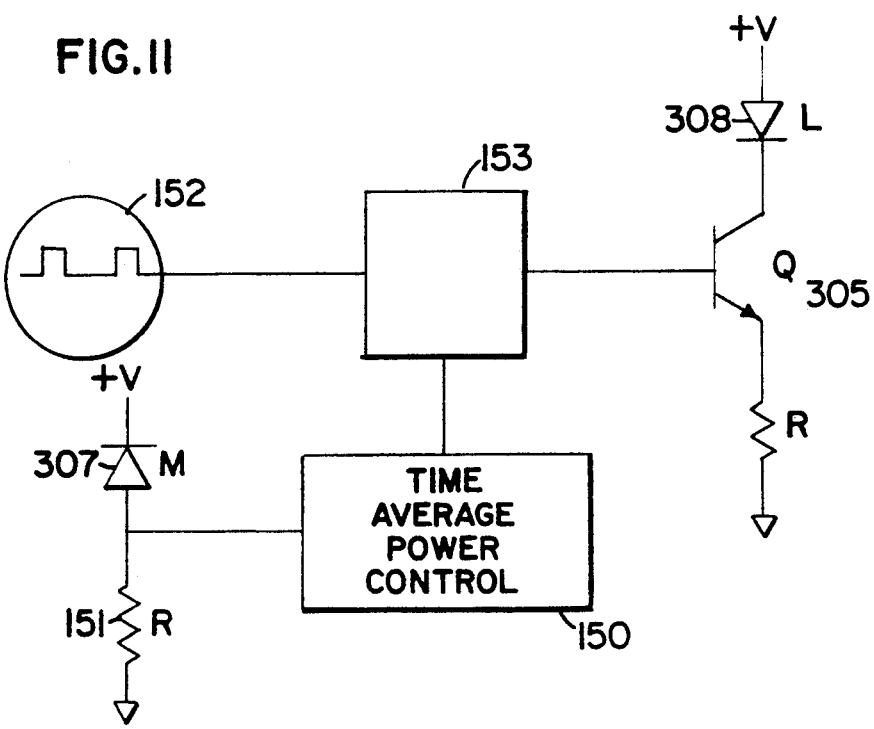
FIG. 11 is a functional block diagram of a modulating laser supply.

An example of a pulsed laser circuit is illustrated in FIG. 11. The circuit works briefly as follows: function circuit block 150 measures the monitor detector feedback current into resistor 151. It then converts this into a time average DC signal to adjust for long term lifetime power output control. Circuit 152 creates a waveform of the desired nature to control the pulsing (the waveform may be either a square wave as illustrated, or sinusoidal among others). Functional block 153 monitors blocks 150 and 152 to control transistor 305 which controls the output light signal of laser diode 308.

I. Alternative Embodiment

In FIG. 12, there is illustrated an alternative embodiment to the present invention. The counter electronics 100 remains the same, as discussed in connection with the counter 20 above. The location of detector means 60, and the elimination of flat mirror 22 is affected. Therefore, the incremental step distance of the laser beam 50 down the longitudinal length of cylindrical mirrors 21a, 21b must be reduced such that consecutive incremental steps on each of the cylindrical mirrors 21 are proximate one another, rather than leaving a gap to be filled in by the beam 50 second set of incremental steps.

Also, cylindrical mirrors 21a and 21b could be replaced by flat mirrors to reduce production expenses. Additionally, single particle detection using extinction techniques may be accomplished through use of a single or plurality of straight beams directly into detector devices.

While several particular embodiments of the invention have been described with respect to their application for detecting single particles intersecting a sheet of light, it will be understood by those skilled in the art that the invention is not limited to such application or embodiment or to the particular circuits disclosed and described herein. It will be appreciated by those skilled in the art that other circuit configurations that embody the principles of this invention and other applications therefor other than as described herein can be configured within the spirit and intent of this invention. The circuit configurations, beam shaping optics, beam steering means, positive or negative logic and mirrors utilized all as described herein are provided only as examples of embodiments that incorporate and practice the principles of this invention. Other modifications and alterations are well within the knowledge of those skilled in the art and are to be included within the broad scope of the appended claims.

We claim:

1. An apparatus for detecting particles in a fluid environment comprising:
   (a) means for providing a light beam having a defined axis;
   (b) lens means for receiving and shaping said light beam to provide a collimated beam having a predetermined width and height;
   (c) first mirror means having a first surface for providing multiple reflections of said light beam;
   (d) second mirror means having a second surface for providing multiple reflections of said light beam that is reflected from said first surface;
   (e) said first and second surfaces being spatially oriented substantially parallel in space from each other wherein the distance between the adjacent points of reflection on each of said first and second surfaces is substantially twice the width of said light beam;
   (f) third mirror means, arranged and cooperatively configured between said first and second mirror means, for reflecting said light beam from said first mirror means onto said second mirror means after said beam of light reflects between said first and second mirror means a first set of times, wherein said light beam reflects a second set of times between said first and second mirror means, whereby a sheet of light is created between said first and second mirror means; and
   (g) photodetector means for detecting light intensity decreases caused by light extinguished from said light beam by a particle intersecting said sheet of light.

2. The apparatus as recited in claim 1, wherein said first mirror means and said second mirror means comprise mirrors curved to reduce the divergence of said light beam.

3. The apparatus as recited in claim 1, wherein said reflections on said first and second surfaces have angles of incidence which are less than or equal to 30 degrees.

4. The apparatus as recited in claim 1, wherein said means for providing a beam of light comprises a laser diode.

5. The apparatus as recited in claim 1, wherein said first mirror means and said second mirror means each comprise flat mirrors.

6. The apparatus as recited in claim 1, wherein said lens means includes a lens having a focal length selected to compensate for beam divergence, said lens positioned spatially between said means for providing a light beam and said first mirror means.

7. An apparatus for detecting particles in a fluid, of the type wherein a sample fluid passes through a beam of light, and wherein particles in the fluid remove light from the beam when the particles intersect the beam, the apparatus comprising:
   (a) a source of light to provide a focused beam;
   (b) deflecting means for deflecting the light through a sensing volume, the sensing volume being defined by the intersection of the fluid and the beam wherein said deflecting means includes:
      (i) oppositely disposed first and second reflective surfaces for incrementally stepping the point of reflection of light on said reflective surfaces through the sensing volume; and
      (ii) third reflecting means, cooperatively arranged and configured in relation to said first and second reflective surfaces, for reflecting the beam back into the sensing volume, wherein the light steps back through the sensing volume between said first and second reflective surfaces in second incremental steps, whereby a sheet of light is formed covering the sensing volume;
   (c) detector means for detecting changes in the intensity of the light after the light has intersected the sensing volume, said detector means arranged and configured wherein the light is operatively incident on said detector means, wherein the removal of light by particles intersecting the sensing volume causes changes in the intensity of light incident on said detector means and whereby said detector means detect particles as corresponding changes in light intensity; and
   (d) modulating means, cooperatively connected to said source of light, for modulating said source of light, wherein the light operatively incident on said detector means is modulated at a frequency above said detector means detection limits.

8. A method for detecting single particles in a fluid, the method comprising the steps of:
   (a) generating a source of collimated light;
   (b) deflecting the light through a sensing volume, the sensing volume being defined by the intersection of the fluid and the light by reflecting the light back and forth between first and second reflective surfaces arranged and configured about the sensing volume; and
   (c) detecting changes in the intensity of the light after the light has intersected the sensing volume, said detector means arranged and configured wherein the light is incident on said detector means and wherein the extinction of light by particles intersecting the sensing volume causes changes in the intensity of light incident on said detector means, whereby said detector means detect the particle as a corresponding decrease in light intensity.

* * * * *